United States Patent [19]
Remenyik et al.

[11] Patent Number: 5,877,008
[45] Date of Patent: Mar. 2, 1999

[54] MICROINJECTOR FOR BLASOCYSTS

[75] Inventors: Carl J. Remenyik, Knoxville, Tenn.;
Richard P. Woychik, Beechwood, Ohio; David R. Patek, Loudon, Tenn.;
James A. Hawk, Oak Ridge, Tenn.;
John C. Turner, Clinton, Tenn.

[73] Assignee: Lockheed Martin Energy Research Corporation, Oak Ridge, Tenn.

[21] Appl. No.: 898,232

[22] Filed: Jul. 22, 1997

[51] Int. Cl.[6] ..................................................... C12M 3/04
[52] U.S. Cl. .................................... 435/285.1; 435/285.2; 435/286.2; 73/864.23; 73/864.25; 935/53; 935/85
[58] Field of Search ............................. 435/285.1, 285 R, 435/286 Z; 73/864.23, 864.24, 864.25; 350/530, 531; 935/53, 85

[56] References Cited

U.S. PATENT DOCUMENTS 5,114,854   5/1992   Bertholdt ............................. 435/240.1

OTHER PUBLICATIONS

C. L. Stewart, "Production of Chimeras between Embryonic Stem Cells and Embroys," in *Methods of Enzymology*, vol. 225, Academic Press, San Diego, (Title. of vol. 225 Guide to Techniques in Mouse Development by P. M. WAssarman and M. L. DePamphilis). 1993, pp. 823–855.

*Primary Examiner*—David A. Redding
*Attorney, Agent, or Firm*—James M. Spicer

[57] ABSTRACT

An electromechanical device for driving the tip of a microinjection cannula, or needle, through the outer barrier of a blastocyst, cell, or cell nucleus for the injection of cells or other bioactive materials. Either a flexible frame or a ram moving within a base member is employed. Cannula motion is achieved by means of a piezoelectric stack and spring return system. The thrust motion over a predetermined microscopic distance is achieved without cannula setback prior to the thrust movement. Instead of specially prepared beveled and tipped needles, standard unimproved cannulas or needles can be used.

14 Claims, 6 Drawing Sheets

MICROINJECTOR FOR BLASOCYSTS

The United States Government has rights in this invention pursuant to contract no. DE-AC05-96OR22464 between the United States Department of Energy and Lockheed Martin Energy Research Corporation.

FIELD OF THE INVENTION

The present invention relates to the field of genetic engineering, and more specifically to an electromechanical apparatus for abruptly driving the tip of a microinjection cannula or needle through the wall of a blastocyst, cell, cell nucleus, etc., for the injection of cells or other bioactive materials thereinto.

BACKGROUND OF THE INVENTION

The production of mice with specific mutations is an important and frequently applied procedure that is used to determine the function of individual genes. For example, genetically altered stem cells are frequently injected into mouse blastocysts by means of cannulas, sharpened needles, or other injection means. The rate at which such injection processes can be performed is severely limited by the time-consuming and intricate production of microinjection needles with which to inject the cells into the blastocysts. In current practice, standard cannulas or needles are converted to injection needles having tips that first must be beveled and then pointed. The fabrication of these improved needles is largely an art requiring experienced technicians and many tedious steps. The inevitable result is that needles are produced that are disturbingly nonuniform. This nonuniformity in turn makes the injection step more demanding, and is a significant impediment to automation. In addition to being time consuming, the lengthy fabrication process also results in many rejects. At times, the defectiveness of the needle becomes apparent only after the whole system, cells and blastocyst are prepared, and the operator attempts an injection under the microscope.

In addition to the above problems caused by having to manually prepare beveled and tipped needles, the manner in which the blastocyst injection step is carried out presents additional difficulties. Typically, the injection is done on the stage of an inverted microscope. There are usually one or more micromanipulators rigidly attached to the microscope. These are used to manipulate the biological materials and perform other operations. The micromanipulators typically have a set of three motors used for coarse positioning, and a hydraulic actuator operated from a joystick that is used for fine positioning. The micromanipulators have been developed to the point where they are capable of positioning the tip of the needle at the blastocyst wall very well. It is also known to employ a computer to return the injection needle to a previous microposition after it has been withdrawn.

The injection step is usually carried out manually with a micromanipulator. The usual practice is for the operator to position the injection needle at the wall of the blastocyst, pull the needle back out of sight from the viewing field of the microscope in order to allow enough distance to accelerate the needle, and then slap the handle of the micromanipulator forward to jam the needle tip into the blastocyst. If the hand of the operator does not move along a sufficiently straight line, the blastocyst may be missed, knocked away, or torn and destroyed by the sharp needles. These attempts to use micromanipulators for the injection step have thus generally been unsatisfactory. No micromanipulators are known that are capable of carrying out the precise thrusting motion over the requisite microscopic distance needed to achieve proper cell injection.

In the above-described injection methods, a further complicating aspect is that of stopping the advance of the injection needle a predetermined distance into the blastocyst. A fully satisfactory solution to this problem has not been achieved by the known methods either.

SUMMARY OF THE INVENTION

Accordingly, it is a principal object of the present invention to provide a blastocyst microinjector suitable for attachment to a micromanipulator, the micromanipulator capable of functioning in the usual way to cause a microinjection cannula or needle to be carefully positioned against a blastocyst wall, and the microinjector capable of thrusting the cannula or needle through the blastocyst wall a predetermined microscopic distance.

Another object of the present invention is to provide a microinjector for blastocyst penetration that uses the blunt needles that are produced automatically by existing instruments, and from which the currently used needles are fabricated.

Another object of the present invention is to provide a microinjector for blastocyst penetration that is capable of abruptly thrusting the injection cannula or needle through the blastocyst wall a predetermined microscopic distance without requiring any cannula setback prior to the thrust motion.

In accordance with a first preferred embodiment of the present invention, there is provided an apparatus for advancing a microinjection cannula into a target comprising: a rectangular frame, the frame comprising a base, identical front and rear flexure bars located opposite each other, and a spacer bar located opposite the base; a cannula holder detachably mounted to the spacer bar, the cannula holder adapted to hold a microinjection cannula such that the axis of the microinjection cannula is parallel to the spacer bar, and is in the plane of the frame; a housing attached to the base, the housing extending outside the frame, the housing containing a spring for applying a force between the housing and the rear flexure bar at a location on the rear flexure bar near the spacer bar; and a piezoelectric actuator disposed between the base and the rear flexure bar for applying a force between the base and the rear flexure bar at a location on the rear flexure bar opposite the spring such that the microinjection cannula is advanced along the cannula axis into the target when the piezoelectric actuator is discharged.

In accordance with a second preferred embodiment of the present invention, there is provided an apparatus for advancing a microinjection cannula into a target comprising: a base; a ram movable within the base along a single axis; a cannula holder detachably mounted to the ram, the cannula holder adapted for holding a microinjection cannula such that the axis of the microinjection cannula is parallel to the single axis; springs disposed between the base and the ram for applying a force between the base and the ram; and piezoelectric actuators disposed between the base and the ram opposite the springs for applying an opposite force between the base and the ram such that the microinjection cannula is advanced along the cannula axis into the target when the piezoelectric actuators are discharged.

In accordance with a third preferred embodiment of the present invention, there is provided an apparatus for advancing a microinjection cannula into a target comprising: a rectangular frame, the frame comprising a base, identical front and rear flexure bars located opposite each other, and a spacer bar located opposite the base; a cannula holder detachably mounted to the spacer bar, the cannula holder adapted to hold a microinjection cannula such that the axis of the microinjection cannula is parallel to the spacer bar, and is in the plane of the frame; a housing attached to the base, the housing extending outside the frame, the housing containing a piezoelectric stack for applying a force between the housing and the rear flexure bar at a location on the rear flexure bar near the spacer bar; and a spring disposed between the base and the rear flexure bar for applying a force between the base and the rear flexure bar at a location on the rear flexure bar opposite the piezoelectric stack such that the microinjection cannula is advanced along the cannula axis into the target when the piezoelectric actuator is charged.

In accordance with a fourth preferred embodiment of the present invention, there is provided an apparatus for advancing a microinjection cannula into a target comprising: a base; a ram movable within the base along a single axis; a cannula holder detachably mounted to the ram, the cannula holder adapted for holding a microinjection cannula such that the axis of the microinjection cannula is parallel to the single axis; springs disposed between the base and the ram for applying a force between the base and the ram; and piezoelectric actuators disposed between the base and the ram opposite the springs for applying an opposite force between the base and the ram such that the microinjection cannula is advanced along the cannula axis into the target when the piezoelectric actuators are charged.

DETAILED DESCRIPTION OF THE INVENTION

FIRST PREFERRED EMBODIMENT

Figure 1:
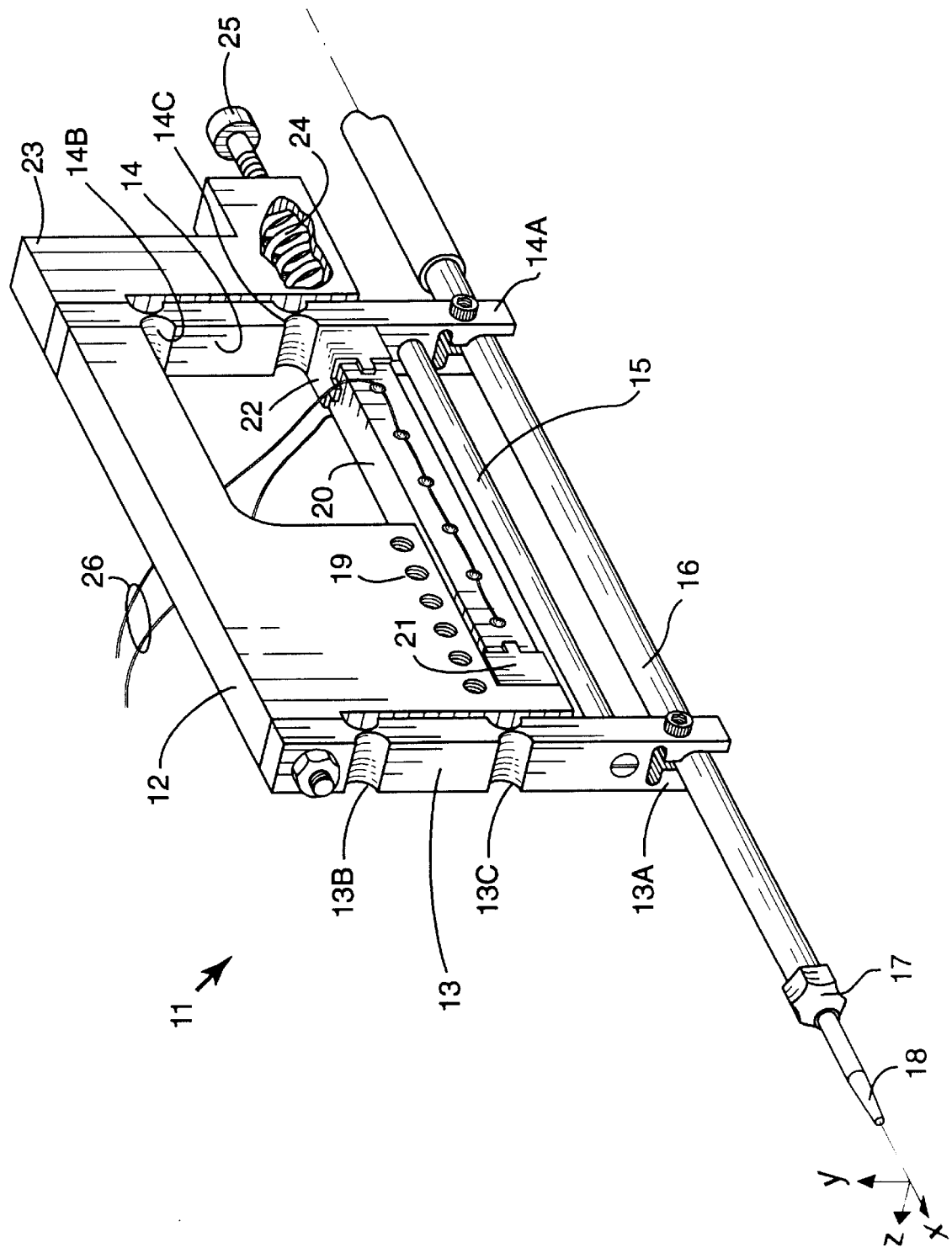
FIG. 1 is a perspective view of a first embodiment of the present invention featuring flexure pivot movement.

FIG. 1 shows a microinjector 11 according to a first preferred embodiment of our invention. Tapped holes 19 are provided as a means of attaching the microinjector 11 to the moving arm of a micromanipulator that is in turn attached to a microscope, as previously described.

In FIG. 1, reference numeral 18 refers to the cannula, micropipette, or needle, etc., which is used to penetrate a target blastocyst, cell, cell nucleus, early living embryo, etc. In this and all the other embodiments of our invention, the cannula 18 is affixed to a tubular holder 16 by means of a gland 17. The tubular holder 16 can be a standard commercial product (for example, a stainless steel tube) and it may contain the material to be injected into the target blastocyst, cell, cell nucleus, etc.

In FIG. 1 and all the other embodiments of our invention, a right-handed orthogonal reference system has X, Y, Z coordinates, as shown. The positive and negative X-directions are referred to as forward and backward directions respectively. The positive and negative Y-directions are referred to as up and down, respectively. The Z-directions are referred to as lateral, without distinction of the positive and negative directions because the device is symmetrical in these directions, i.e., with respect to the X-Y plane.

The microinjector 11 of FIG. 1 is configured as a rectangular frame comprised of four parts rigidly attached at their ends to each other. The four parts of the rectangular frame are a base 12, identical front and rear flexure bars 13, 14 located opposite each other, and a spacer bar 15 located opposite the base 12. The base 12 contains the tapped holes 19 for mounting to the micromanipulator of the microscope.

The ends of the flexure bars 13, 14 at the spacer bar 15 extend and are configured as clamps 13A, 14A to grip the tubular holder 16. By this means, the tubular holder 16 is arranged to lie in the plane of the frame (the X-Y plane) and is axially arranged in the x-direction. In order for the cannula 18 to move microscopically along its axis (the X axis), material is removed from the front and rear flexure bars 13, 14 at two locations to provide two identical flexure pivots in each bar (13B, 13C, and 14B, 14C, respectively). The pivots in the bars 13, 14 allow the spacer bar 15 and tubular holder 16 to move in the X direction relative to the fixed base 12 with minimal movement in the Y direction. The rectangular frame arrangement permits movement of the cannula in the X direction due to flexing of the frame at the flexure joints, but acts to prevent movement of the cannula in the Y and Z directions.

The manner of moving the frame members 13, 14, 15 with respect to the fixed base 12 in order to achieve the desired movement of the cannula 18 is as follows. A piezoelectric stack 20 is affixed between the base 12 and rear flexure bar 14 by means of insulating supports 21, 22 attached to the base 12 and rear flexure bar 14, respectively. The piezoelectric stack 20 is located parallel to spacer bar 15 and close to it. In order to achieve this placement of the stack 20, a portion of the base 12 close to the front flexure bar 13 is made to extend within the frame almost to the spacer bar 15.

A housing 23 containing a spring 24 therewithin is attached to the frame at the location where the base 12 and rear flexure bar 14 attach to one another. The housing 23 is located outside the frame and extends parallel to the flexure bar 14 to the piezoelectric stack 20. The spring 24 is arranged within housing 23 to press against flexure bar 14 at a location directly opposite the piezoelectric stack 20. A spring tensioning bolt 25 located in the housing 23 is used to adjust the pressure of the spring 24 against the flexure bar 14.

In operation, voltage is applied to leads 26, which causes the piezoelectric stack 20 to charge and expand in length. As it expands, the stack 20 moves the flexure bar 14 against the spring 24, simultaneously drawing the tubular holder 16 and its cannula 18 in the negative x-direction. With the needle 18 in this retracted position, the needle tip is micromanipulated into the desired position with respect to the blastocyst wall (usually touching the wall). Penetration into the blastocyst is achieved by rapidly removing the charge from the piezoelectric stack 20. When the charge is removed, the stack 20 rapidly contracts to its original length. This action, together with the spring force, immediately accelerates the flexure bar 14 in the positive x-direction, in turn causing the tubular holder 16 and its attached cannula 18 to abruptly move in the positive x-direction the precise microdistance needed for the cannula 18 to penetrate the blastocyst successfully.

In contrast to the present methods of blastocyst penetration that require a setback of the cannula out of the field of view of the microscope, it will be appreciated that this embodiment of our invention (and all the other embodiments as well) involve no cannula setback at all. Rather, the cannula may be placed as close to the target blastocyst as desired, and the only motion that is produced is the abrupt forward movement of the cannula into the blastocyst made possible by the simultaneous fast action of the spring 24 and the even faster withdrawal of the piezoelectric stack 20 from the spring 24 upon charge removal. In this and all the embodiments of our invention, the precise forward movement is determined by the contraction of the piezo elements in the stack 20. The travel distance of the microinjection cannula is continuously variably determined by the magnitude of the applied potential difference, or voltage.

SECOND PREFERRED EMBODIMENT

Figure 2:
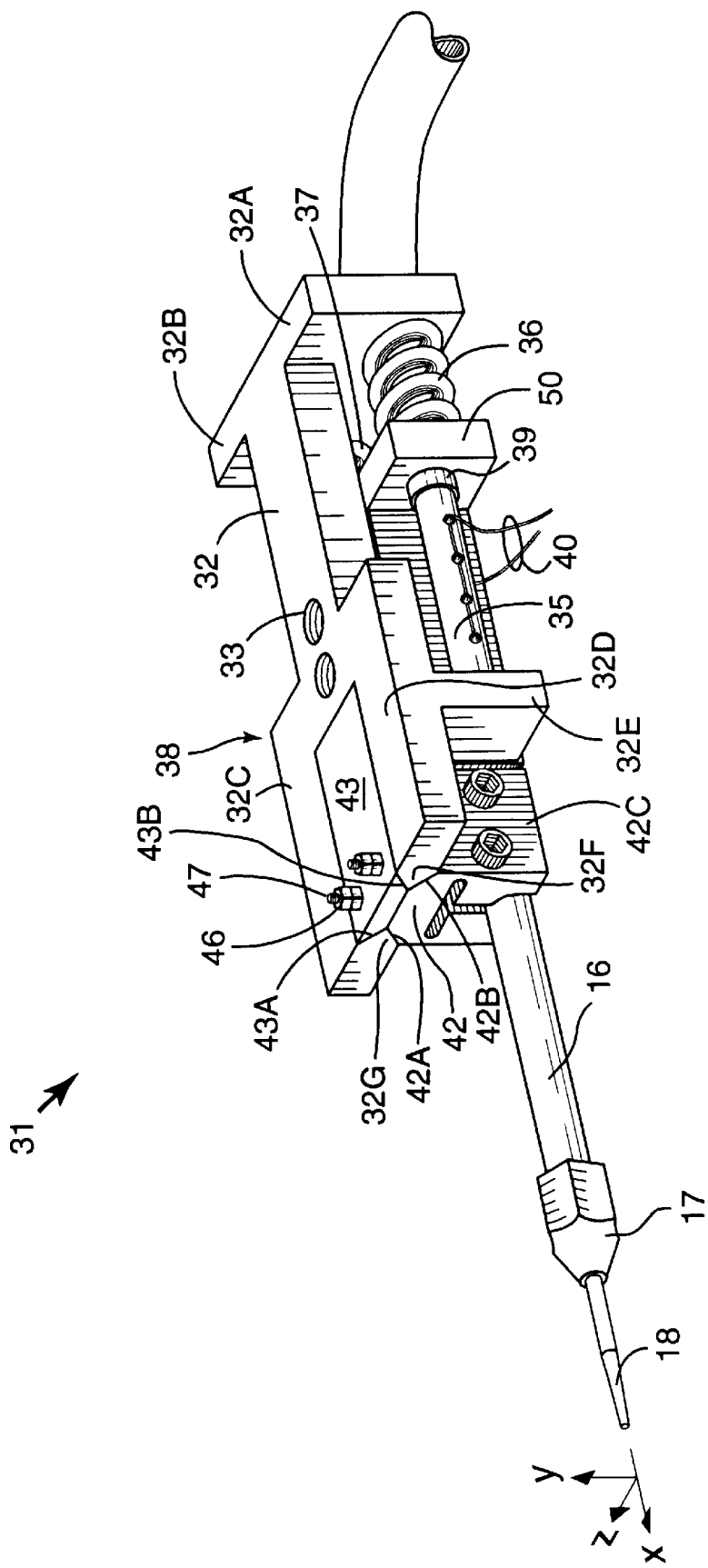
FIG. 2 is a perspective view of a second embodiment of the present invention featuring sliding wedge movement.

FIG. 2 shows a microinjector 31 according to a second preferred embodiment of our invention. In FIG. 2, the tubular holder 16, gland 17, and cannula 18 are the same as described for the embodiment of FIG. 1.

The microinjector 31 comprises a generally rectangular base 32 and a ram 42 slidably fitted in the base 32. The rectangular base 32 has tapped holes 33 used to attach the base 32 to the moving arm of a micromanipulator mounted on a microscope. The base 32 extends at one end laterally in both Z-directions to form a support cross bar 32A, 32B for two springs 36, 37. At its opposite end, the base 32 divides, again laterally in both z-directions, into a fork-shaped retainer 38 having two arms 32C, 32D. The underside of each arm 32C, 32D of the retainer 38 extends in the negative y-direction to form two plates, one of which (32E) is visible in FIG. 2. These plates serve as abutments for two piezoelectric stacks, one of which (35) is visible in FIG. 2.

The ram 42 is made slidably movable in the x-direction within the arms 32C, 32D of the fork-shaped retainer 38 in the following manner. The inner surfaces of the arms 32C, 32D of the fork-shaped retainer 38 are formed into slanted (wedge-shaped) guide rails 32F, 32G extending in the x-direction. An adjustable guide plate 43 is placed on the top surface of the ram 42, and held in place thereon by means of nuts 46 attached to posts 47. The top surface of the ram 42 and the lower surface of the plate 43 are formed as slanted surfaces (42A, 42B, and 43A, 43B, respectively) for mating with the wedge-shaped guide rails 32F, 32G of the fork-shaped retainer 38. The slanted surface portions of the adjustable guide plate 43 and ram 42 surround the two wedge-shaped guide rails 32F, 32G in such a way that by securing the adjustable guide plate to the ram by means of the threaded poles 47 and adjustment nuts 46, the motion of the ram is restricted to sliding in the direction of the edges of the wedge-shaped guide rails (i.e., the x-direction).

The rear end of the ram 42 (end nearest the support cross bar 32A, 32B) extends laterally in both z-directions into two driver plates with surfaces parallel to the surfaces of the support cross bar 32A, 32B. One of these driver plates (50) is visible in FIG. 2. The forward end of the ram 42 (end beneath the wedge-shaped guide rails 32F, 32G) is configured as a clamp 42C used to grip the tubular holder 16 and its attached cannula 18. The piezoelectric stacks are held in place on the stationary plates 32E and driver plates 50 by means of insulating supports, one of which (39) is visible in FIG. 2. The two springs 36, 37 are clamped between the driver plates 50 on the ram 42 and the support cross bar 32A, 32B on the base 32 coaxially with the two piezoelectric stacks. The axes of the cannula 18, the cannula holder 16, the piezoelectric stacks 35, the springs 36, 37, and the wedge-shaped guide rails 32F, 32G are all parallel. This allows movement of the cannula 18 in the x-direction when the piezoelectric stacks 35 are operated.

In operation, the microinjector 31 assumes its stand-by state when an electric potential difference is applied to the leads 40 of the piezoelectric stacks. The electric potential difference causes the piezoelectric stacks to lengthen. By this means, the piezoelectric stacks force the driver plates 50 of the ram 42 to move in the negative x-direction, and they also compress the springs 36, 37. The displacement of the driver plates 50 simultaneously moves the ram 42, the cannula holder 16, and the microinjection cannula 18 in the negative x-direction.

With the microinjector 31 in the standby state, the operator guides the tip of the microinjection cannula 18 by means of the micromanipulator to touch the target immobilized in the field of view of the microscope. When the cannula 18 assumes the desired position, the operator operates a switch (not shown) by foot or by hand, short-circuiting and discharging the piezoelectric stacks 35. Thereupon, the piezoelectric stacks abruptly contract, the springs 36, 37 expand and thrust forward the ram 42 and microinjection cannula assembly. The sudden movement causes the tip of the cannula 18 to break through the surface barrier of the target. The travel distance of the microinjection cannula is continuously variably determined by the magnitude of the applied potential difference, or voltage.

THIRD PREFERRED EMBODIMENT

Figure 3:
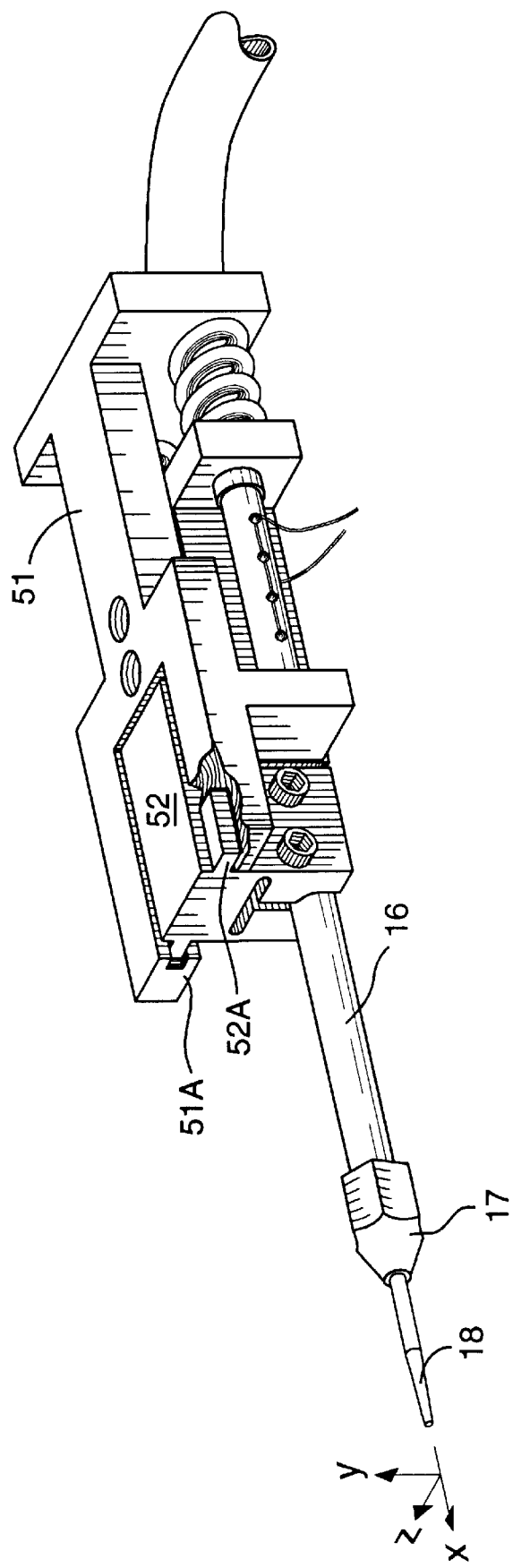
FIG. 3 is a perspective view of a third embodiment of the present invention featuring sliding rectangular bar movement.

FIG. 3 shows a microinjector according to a third preferred embodiment of our invention. The microinjector of FIG. 3 is comprised of a base 51 and ram 52 identical to those described for the embodiment of FIG. 2, except that the guide rails on the fork-shaped retainer of the base are replaced by rectangular grooves 51A, the adjustable guide plate is omitted, and the ram is configured to have two protruding rectangular rails 52A that fit into and are slidable within the two rectangular grooves 51A. The same sliding movement of the ram 52 in the x-direction and the same piezoelectric actuation is used as was used in the FIG. 2 embodiment.

FOURTH PREFERRED EMBODIMENT

Figure 4:
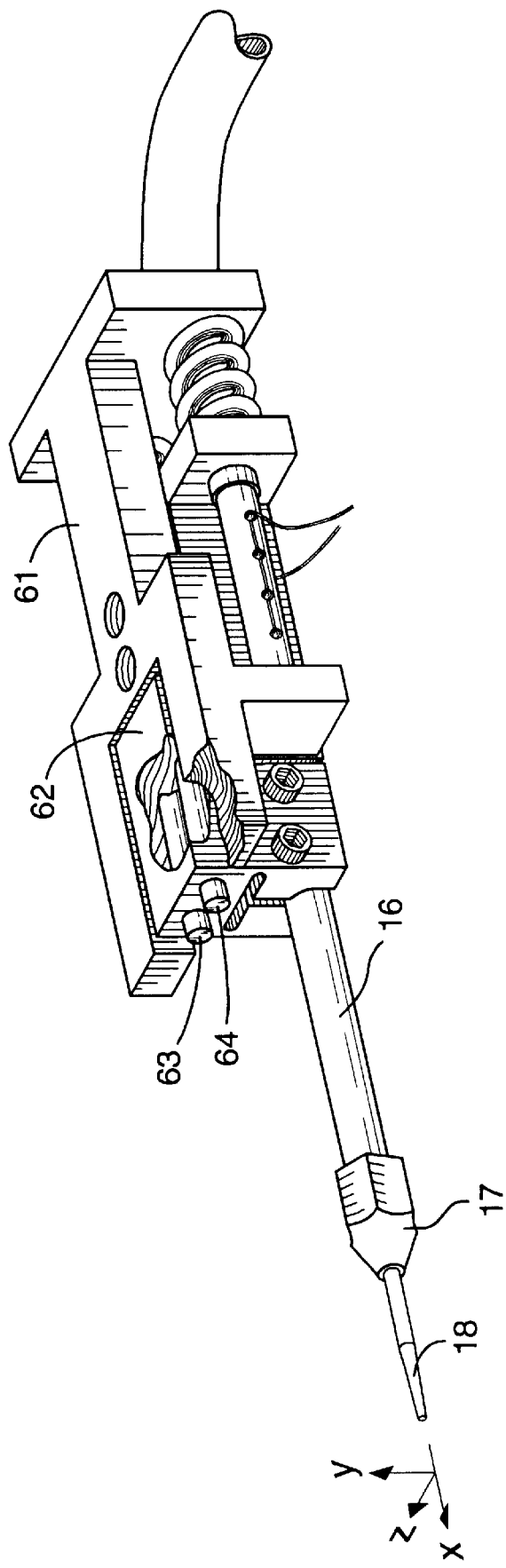
FIG. 4 is a perspective view of a fourth embodiment of the present invention featuring sliding circular bar movement.

FIG. 4 shows a microinjector according to a fourth preferred embodiment of our invention. The microinjector of FIG. 4 is comprised of a base 61 and ram 62 identical to those described for the embodiment of FIG. 2, except for the guiding mechanism between the ram and the arms of the fork-shaped retainer. The arms of the fork-shaped retainer and the ram do not touch, and the adjustable guide plate is omitted. The arms of the fork-shaped retainer serve only to hold the abutments for the piezoelectric stacks. Two circular rods 63, 64 are fastened into the base of the fork-shaped retainer with axes parallel to the axis of the cannula 18. The rods extend through two bore holes in the ram, and the ram is slidable in the x-direction on the rods. The same piezoelectric actuation is used as was used in the FIG. 2 embodiment.

FIFTH PREFERRED EMBODIMENT

Figure 5:
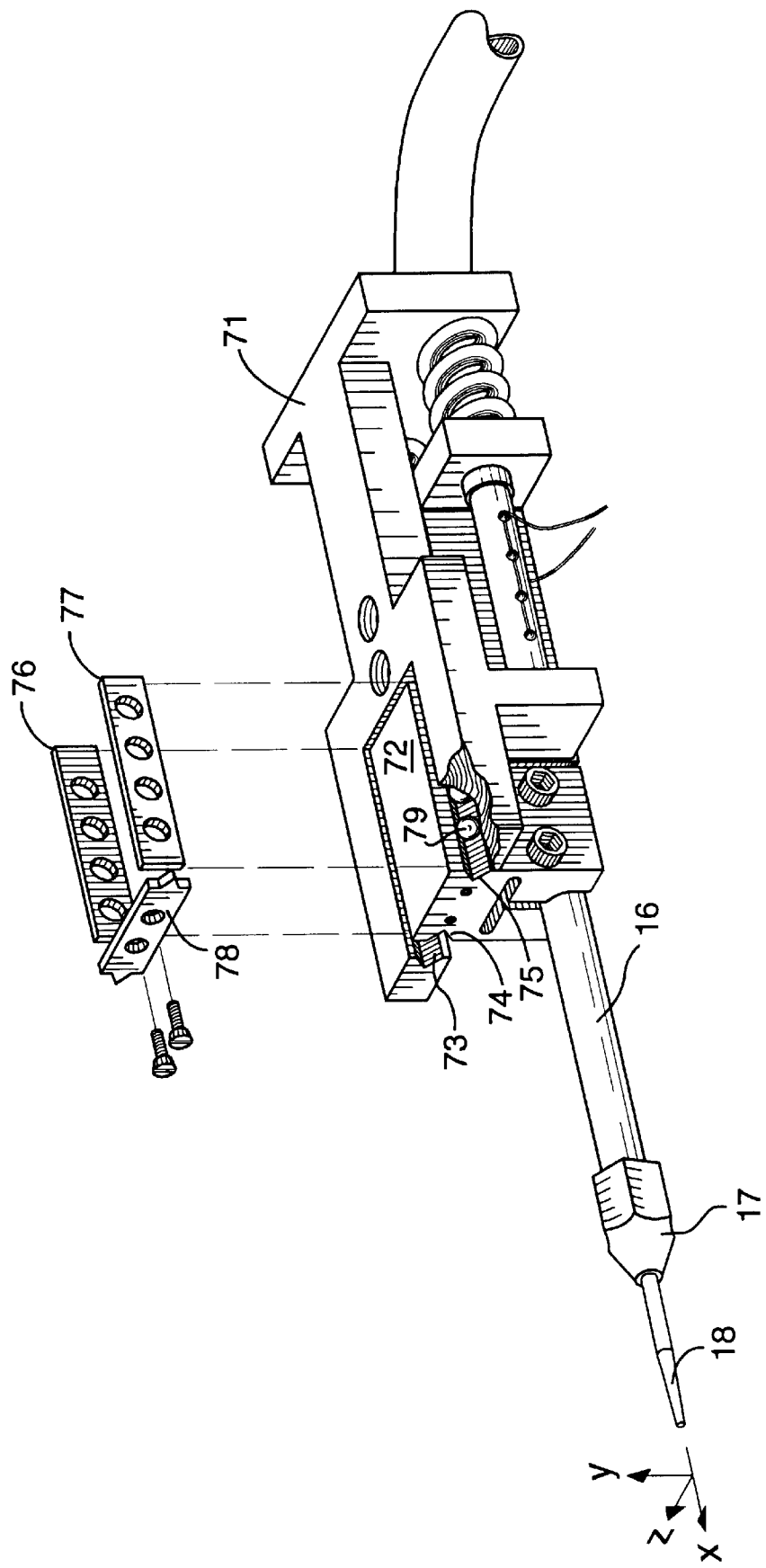
FIG. 5 is a perspective view of a fifth embodiment of the present invention featuring ball bearing movement.

FIG. 5 shows a microinjector according to a fifth preferred embodiment of our invention. The microinjector of FIG. 5 is comprised of a base 71 and ram 72 identical to those described for the embodiment of FIG. 2, except for the guiding mechanism between the ram and the arms of the fork-shaped retainer. Guide grooves are cut into the inner sides of each arm of the fork-shaped retainer parallel to the axis of the cannula 18. One guide groove 73 is visible in FIG. 5. Similar guide grooves 74, 75 cut into the sides of the ram 72 face the grooves in the arms of the fork-shaped retainer. Together, these grooves form two channels into which steel balls 79 appropriate for ball bearings are inserted.

Two spacer plates 76, 77 occupy the gaps between the ram and the arms of the fork. The steel balls 79 are in the holes of the spacer plates, and thus even distribution of the balls along the grooves is assured. A retainer plate 78 attached to the face of the ram by means of screws prevents the spacer plates from sliding out from between the ram and the arms of the fork. This configuration permits the ram to roll on the steel balls in the direction of the axis of the microinjection cannula 18, and restricts the ram's motion to the x-direction.

SIXTH PREFERRED EMBODIMENT

Figure 6:
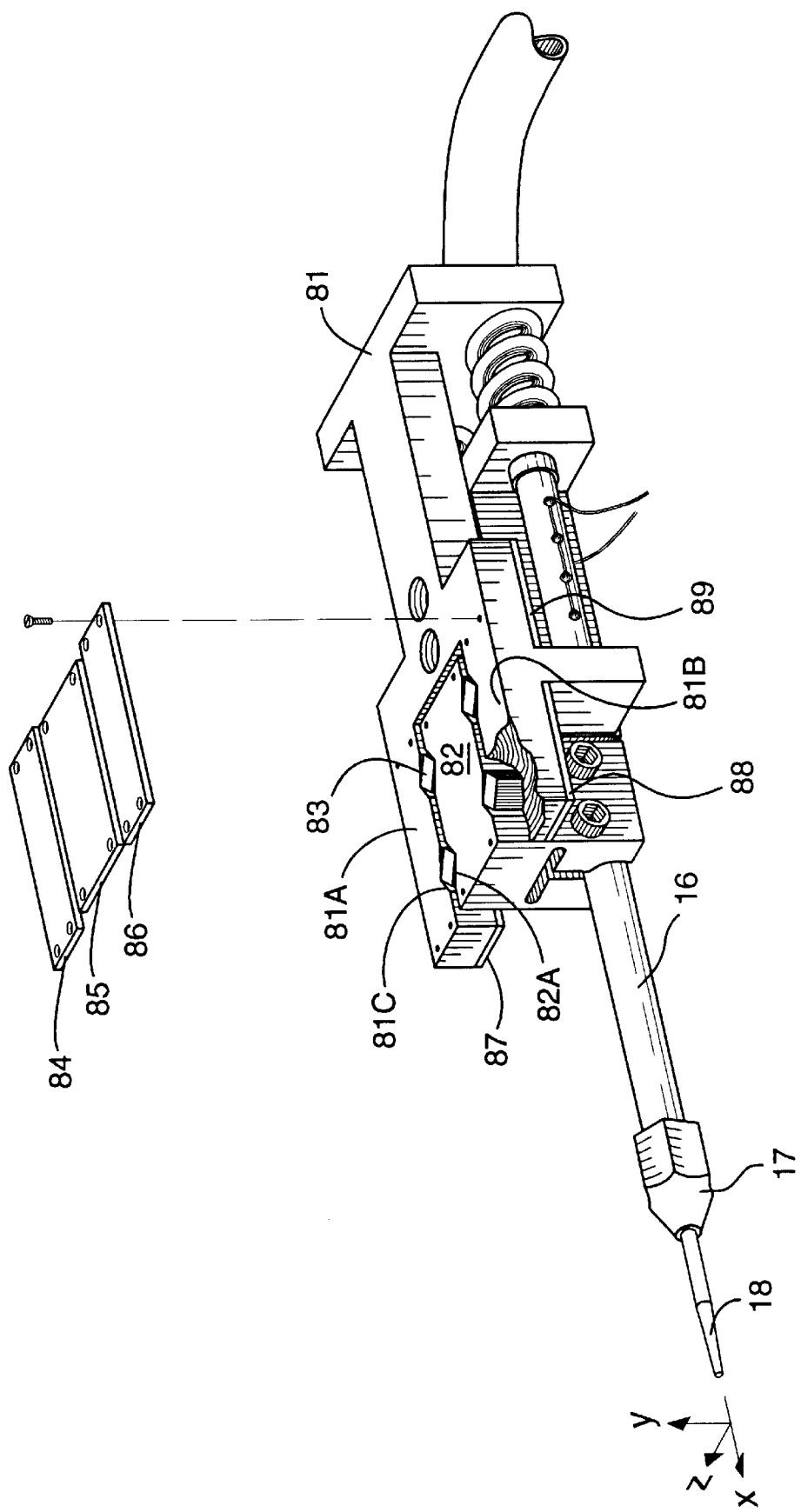
FIG. 6 is a perspective view of a sixth embodiment of the present invention featuring rocking prism movement.

FIG. 6 shows a microinjector according to a sixth preferred embodiment of our invention. The microinjector of FIG. 6 is comprised of a base 81 and ram 82 identical to those described for the embodiment of FIG. 2, except for the suspension of the ram within the arms 81A, 81B of the fork-shaped retainer. Two guide grooves 81C are cut into the inner sides of each arm of the fork-shaped retainer. The direction of the axes of these guide grooves is perpendicular to the axis of the microinjection cannula 18, that is, the guide grooves are parallel to the y-axis. Similar guide grooves 82A are cut into opposite sides of the ram 82. They face the guide grooves 81C in the arms of the fork-shaped retainer.

Four rods 83, referred to as prismatic in shape, are inserted into the channels formed by the guide grooves 81C, 82A facing each other. The four prismatic rods 83 act as pivots between the base 81 and ram 82. The angles enclosed between the faces of the guide grooves are larger than the angles enclosed between the sides of the prismatic pivots. This configuration permits the prismatic pivots to rock in the guide grooves in the direction of the axis of the microinjection cannula 18 (the x-axis). Cover plates 84–89 screwed to the arms of the fork or the ram retain the prismatic pivots in their grooves and prevent the ram from sliding out from between the arms of the fork.

In all of the above embodiments of our invention, if an electric current source providing a sufficiently large short-time current burst is available, the locations of the piezoelectric stacks and the springs can be reversed. When this is done, the manner of operation is also changed. The piezoelectric stacks are in the discharged and contracted state when the device is in the stand-by state. The abrupt thrusting motion of the cannula into the blastocyst is induced by the surge of electric current charging the piezoelectric stacks.

While there has been shown and described what is at present considered the preferred embodiments of the invention, it will be obvious to those skilled in the art that various changes and modifications may be made therein without departing from the scope of the invention as defined by the appended claims.

We claim:

1. An apparatus for advancing a microinjection cannula into a target comprising:

a rectangular frame, said frame comprising a base, identical front and rear flexure bars located opposite each other, and a spacer bar located opposite said base;

a cannula holder detachably mounted to said spacer bar, said cannula holder adapted to hold a microinjection cannula such that the axis of the microinjection cannula is parallel to said spacer bar, and is in the plane of said frame;

a housing attached to said base, said housing extending outside said frame, said housing containing a spring for applying a force between said housing and said rear flexure bar at a location on said rear flexure bar near said spacer bar; and a piezoelectric actuator disposed between said base and said rear flexure bar for applying a force between said base and said rear flexure bar at a location on said rear flexure bar opposite said spring such that said microinjection cannula is advanced along the cannula axis into said target when said piezoelectric actuator is discharged.

2. An apparatus for advancing a microinjection cannula into a target comprising:

a base;

a ram movable within said base along a single axis;

a cannula holder detachably mounted to said ram, said cannula holder adapted for holding a microinjection cannula such that the axis of the microinjection cannula is parallel to said single axis;

springs disposed between said base and said ram for applying a force between said base and said ram; and piezoelectric actuators disposed between said base and said ram opposite said springs for applying an opposite force between said base and said ram such that said microinjection cannula is advanced along the cannula axis into said target when said piezoelectric actuators are discharged.

3. The apparatus of claim 2 wherein said ram is movable within said base along wedge-shaped guide rails.

4. The apparatus of claim 2 wherein said ram is movable within said base along rectangular rails.

5. The apparatus of claim 2 wherein said ram is movable within said base along circular rods.

6. The apparatus of claim 2 wherein said ram is movable within said base on ball bearings.

7. The apparatus of claim 2 wherein said ram is movable within said base on prismatic pivots.

8. An apparatus for advancing a microinjection cannula into a target comprising:

a rectangular frame, said frame comprising a base, identical front and rear flexure bars located opposite each other, and a spacer bar located opposite said base;

a cannula holder detachably mounted to said spacer bar, said cannula holder adapted to hold a microinjection cannula such that the axis of the microinjection cannula is parallel to said spacer bar, and is in the plane of said frame;

a housing attached to said base, said housing extending outside said frame, said housing containing a piezoelectric stack for applying a force between said housing and said rear flexure bar at a location on said rear flexure bar near said spacer bar; and a spring disposed between said base and said rear flexure bar for applying a force between said base and said rear flexure bar at a location on said rear flexure bar opposite said piezoelectric stack such that said microinjection cannula is advanced along the cannula axis into said target when said piezoelectric actuator is charged.

9. An apparatus for advancing a microinjection cannula into a target comprising:

a base;

a ram movable within said base along a single axis;

a cannula holder detachably mounted to said ram, said cannula holder adapted for holding a microinjection cannula such that the axis of the microinjection cannula is parallel to said single axis;

springs disposed between said base and said ram for applying a force between said base and said ram; and piezoelectric actuators disposed between said base and said ram opposite said springs for applying an opposite force between said base and said ram such that said microinjection cannula is advanced along the cannula axis into said target when said piezoelectric actuators are charged.

10. The apparatus of claim 9 wherein said ram is movable within said base along wedge-shaped guide rails.

11. The apparatus of claim 9 wherein said ram is movable within said base along rectangular rails.

12. The apparatus of claim 9 wherein said ram is movable within said base along circular rods.

13. The apparatus of claim 9 wherein said ram is movable within said base on ball bearings.

14. The apparatus of claim 9 wherein said ram is movable within said base on prismatic pivots.

* * * * *

UNITED STATES PATENT AND TRADEMARK OFFICE
CERTIFICATE OF CORRECTION

PATENT NO. : 5,877,008
DATED : March 2, 1999
INVENTOR(S) : Carl J. Remenyik, Richard P. Woychik, David R. Patek, James A. Hawk and John C. Turner It is certified that error appears in the above-identified patent and that said Letters Patent is hereby corrected as shown below:

On the Title Page:

Item [54] change "MICROINJECTOR FOR BLASOCYSTS" to -- MICROINJECTOR FOR BLASTOCYSTS--

Column 1, line 1, replace "BLASOCYSTS" with --BLASTOCYSTS

Signed and Sealed this

Twenty-seventh Day of March, 2001

*Attest:*

NICHOLAS P. GODICI

*Attesting Officer*    Acting Director of the United States Patent and Trademark Office